(12) United States Patent
Kaneko et al.

(10) Patent No.: US 11,162,940 B2
(45) Date of Patent: Nov. 2, 2021

(54) METHOD FOR SUPPRESSING NONSPECIFIC SIGNALS FROM CONTAMINANTS IN AN IMMUNOASSAY USING SURFACE PLASMON-FIELD ENHANCED FLUORESCENCE SPECTROSCOPY (SPFS)

(71) Applicant: Konica Minolta, Inc., Tokyo (JP)

(72) Inventors: Tomonori Kaneko, Hachioji (JP); Takeshi Isoda, Sayama (JP)

(73) Assignee: KONICA MINOLTA, INC., Tokyo (JP)

( * ) Notice: Subject to any disclaimer, the term of this patent is extended or adjusted under 35 U.S.C. 154(b) by 789 days.

(21) Appl. No.: 14/649,770

(22) PCT Filed: Nov. 8, 2013

(86) PCT No.: PCT/JP2013/080302
§ 371 (c)(1),
(2) Date: Jun. 4, 2015

(87) PCT Pub. No.: WO2014/087802
PCT Pub. Date: Jun. 12, 2014

(65) Prior Publication Data
US 2015/0309019 A1    Oct. 29, 2015

(30) Foreign Application Priority Data

Dec. 5, 2012 (JP) .............................. JP2012-266061

(51) Int. Cl.
*G01N 33/543* (2006.01)
*G01N 33/53* (2006.01)
*G01N 21/64* (2006.01)

(52) U.S. Cl.
CPC ..... *G01N 33/54373* (2013.01); *G01N 21/648* (2013.01); *G01N 21/6428* (2013.01); *G01N 33/5306* (2013.01); *G01N 33/54393* (2013.01); *G01N 2021/6439* (2013.01); *G01N 2333/42* (2013.01); *G01N 2440/38* (2013.01)

(58) Field of Classification Search
CPC ......... G01N 33/54373; G01N 33/5306; G01N 21/6428; G01N 33/54393; G01N 21/648; G01N 2333/42; G01N 2440/38; G01N 2021/6439
See application file for complete search history.

(56) References Cited

U.S. PATENT DOCUMENTS

| | | | |
|---|---|---|---|
| 9,335,324 B2 | 5/2016 | Yamamoto et al. | |
| 10,502,743 B2* | 12/2019 | Isoda | C07K 16/28 |
| 2006/0183217 A1 | 8/2006 | Yanagida et al. | |
| 2007/0110811 A1* | 5/2007 | Lancaster | A61K 38/25 |
| | | | 424/486 |
| 2008/0293147 A1* | 11/2008 | Machida | G01N 33/66 |
| | | | 436/64 |
| 2008/0311676 A1* | 12/2008 | Brate | G01N 33/9493 |
| | | | 436/501 |
| 2009/0269735 A1* | 10/2009 | Imoarai | G01N 33/558 |
| | | | 435/5 |
| 2010/0120057 A1 | 5/2010 | Mehra et al. | |
| 2011/0294141 A1 | 12/2011 | Yamashita et al. | |
| 2012/0196385 A1* | 8/2012 | Yamamoto | G01N 21/6428 |
| | | | 436/529 |
| 2013/0078148 A1* | 3/2013 | Kaya | G01N 21/64 |
| | | | 422/69 |
| 2013/0143332 A1 | 6/2013 | Tsukagoshi et al. | |
| 2014/0170772 A1* | 6/2014 | Ide | G01N 21/648 |
| | | | 436/501 |
| 2015/0276749 A1* | 10/2015 | Isoda | G01N 33/57423 |
| | | | 435/7.23 |
| 2015/0355176 A1* | 12/2015 | Isoda | G01N 33/50 |
| | | | 435/7.4 |

FOREIGN PATENT DOCUMENTS

| | | | |
|---|---|---|---|
| EP | 1650570 A1 | 4/2006 | |
| EP | 2395357 A1 | 12/2011 | |
| JP | S562555 A | 1/1981 | |
| JP | H05188055 A | 7/1993 | |
| JP | H06160390 A | 6/1994 | |

(Continued)

OTHER PUBLICATIONS (Doucet et al. "Development and Validation of an ELISA at Acidic pH for the Quantitative Determination of IL-13 in Human Plasma and Serum", Hindawi Publishing Corporation, Disease Markers, vol. 35 (2013), pp. 465-474) (Year: 2013).*

Extended European Search Report corresponding to Application No. 13859978.2-1408/2930514 PCT/JP2013/080302; dated Apr. 28, 2016.

Japanese Notice of Reasons for Rejection corresponding to Application No. 2014-551007; dated May 9, 2017.

(Continued)

*Primary Examiner* — Tracy Vivlemore
*Assistant Examiner* — Nam P Nguyen
(74) *Attorney, Agent, or Firm* — Cantor Colburn LLP (57) ABSTRACT

Provided is at least one method of suppressing, in an immunoassay using surface plasmon-field enhanced fluorescence spectroscopy (SPFS), nonspecific signals generated by nonspecific adsorption of contaminants contained in a sample to an SPFS sensor section (e.g., a primary antibody, a solid-phase layer and a metal thin film). At least one method relates to a method of suppressing nonspecific signals originating from contaminants in an immunoassay using surface plasmon-field enhanced fluorescence spectroscopy (SPFS) (including cases where a receptor for a compound to be measured is used in place of a primary antibody), the method comprising performing at least one pretreatment.

20 Claims, 2 Drawing Sheets

(56) References Cited

FOREIGN PATENT DOCUMENTS

| | | | |
|---|---|---|---|
| JP | 2590330 B2 | | 3/1997 |
| JP | 2001-074739 A | * | 3/2001 |
| JP | 2001074739 A | | 3/2001 |
| JP | 2001074739 A | * | 3/2001 |
| JP | 2001074739 A1 | * | 3/2001 |
| JP | 2001255325 A | | 9/2001 |
| JP | 2002040023 A | | 2/2002 |
| JP | 2006194746 A | | 7/2006 |
| JP | 2006194746 A1 | | 7/2006 |
| JP | 2012168165 A | | 9/2012 |
| WO | 8908262 A1 | | 9/1989 |
| WO | 2010090264 A1 | | 8/2010 |
| WO | WO2011155435 A1 | * | 12/2011 |
| WO | 2012023391 A1 | | 2/2012 |

OTHER PUBLICATIONS

Written Opinion of the International Searching Authority corresponding to Application No. PCT/JP2013/080302; dated Jan. 21, 2014, with English translation.

International Search Report corresponding to Application No. PCT/JP2013/080302; dated Jan. 21, 2014, with English translation.

Notification of Reason for Refusal for corresponding JP Application No. 2017-134577; dated Apr. 10, 2018.

JPO Notification of Reason for Rejection corresponding to Application No. 2017-134577; dated Nov. 27, 2018.

JP Notification of Reason for Refusal corresponding to Application No. 2019-012105; dated Oct. 23, 2019.

JPO Notice of Reasons of Refusal for corresponding JP Patent Application No. 2019-012105, dated Apr. 21, 2020.

* cited by examiner

METHOD FOR SUPPRESSING NONSPECIFIC SIGNALS FROM CONTAMINANTS IN AN IMMUNOASSAY USING SURFACE PLASMON-FIELD ENHANCED FLUORESCENCE SPECTROSCOPY (SPFS)

CROSS REFERENCE TO RELATED APPLICATIONS

The present U.S. patent application is a U.S. National Phase Application under 35 U.S.C. §371 of International Application PCT/JP2013/080302 filed on Nov. 8, 2013. This application claims a priority under the Paris Convention of Japanese patent application No. 2012-266061 filed on Dec. 5, 2012, the entirety of which is incorporated herein by reference.

TECHNICAL FIELD

The present invention relates to a method of suppressing nonspecific signals originating from contaminants in an immunoassay using surface plasmon-field enhanced fluorescence spectroscopy (SPFS). More particularly, the present invention relates to a method of suppressing, in the above-described immunoassay, nonspecific signals generated by nonspecific adsorption of contaminants contained in a sample to an SPFS sensor section.

BACKGROUND ART

Today, detection and quantification of a tumor marker, a specific protein, other antigen contained in blood or urine of a human or animal or in other biological sample are widely performed for diagnosis in the medical field as well as research in the fields of biology and biochemistry. As a method of specifically detecting a trace amount of a compound to be measured (antigen), an immunoassay is employed. One example thereof is a sandwich method in which an antigen captured by a primary antibody is labeled with a secondary antibody, and a method using a fluorescently labeled antibody or the like as the secondary antibody has been widely performed. There is also known a method in which lectin that binds with a sugar chain of a compound to be measured is labeled and used in place of such a secondary antibody.

In addition, as a method of extremely efficiently excite and highly sensitively detect a fluorescently labeled molecule captured by an antigen-antibody reaction in immunoassay, surface plasmon-field enhanced fluorescence spectroscopy (SPFS) is known. In SPFS, under a condition where attenuated total reflectance (ATR) of an excitation light such as a laser beam irradiated from a light source occurs at the surface of a metal thin film, a surface plasmon (compression wave) is generated from the surface of the metal thin film, thereby the amount of photons included in the excitation light irradiated from the light source is increased by several ten times to several hundred times and an electric field-enhancing effect of the surface plasmon light can be obtained. Further, in an immunoassay using SPFS, by utilizing this electric field-enhancing effect to efficiently excite a fluorescent substance bound with a compound to be measured that is captured in the vicinity of a metal thin film and by observing the thus enhanced fluorescence emission, an infinitesimal amount of the compound can be measured.

Meanwhile, in biological samples such as blood (serum and plasma), in addition to a compound to be measured, a variety of proteins, lipids and other contaminants are contained. In an immunoassay, by nonspecific adsorption of these contaminants to, for example, a primary or secondary antibody or a support for immobilization of an antibody and binding of a fluorescent label to the contaminants, nonspecific signals originating from the contaminants are generated to cause background noise. Particularly, in an immunoassay using SPFS, a sensitivity that is at least 100 times higher than that of an immunoassay using a chemiluminescence method is realized; therefore, nonspecific signals that are not detected by a chemiluminescence method are also detected, and this causes a reduction in the measurement sensitivity. Further, in SPFS, even a small amount of a fluorescent label adhering to a sensor section (e.g., a primary antibody, a solid-phase layer and a metal thin film) via contaminants alters the refractive index and influences the electric field-enhancing effect. Consequently, the background noise of the fluorescence measurement becomes unstable, and this may hinder the high-sensitivity measurement. This problem in SPFS presents a large problem particularly when measuring a crude sample such as serum.

With regard to this problem, as a measure for inhibiting nonspecific adsorption on a sensor area in SPFS, there has been proposed an SPFS sensor chip in which, in a flow channel for SPFS measurement, a purification area and a sensor area are arranged upstream and downstream, respectively, relative to the flow direction (Patent Document 1). In this manner, measures for suppression of nonspecific signals and reduction of background noise in SPFS have already been proposed; however, it is important to select the most effective method in accordance with the sample, compound to be measured, purpose of measurement, operability, cost and the like, and there is thus a demand for further proposals.

PRIOR ART REFERENCE

Patent Document

[Patent Document 1] WO2012/023391

SUMMARY OF THE INVENTION

Problems to be Solved by the Invention

An object of the present invention is to provide a method of suppressing, in an immunoassay using surface plasmon-field enhanced fluorescence spectroscopy (SPFS), nonspecific signals generated by nonspecific adsorption of contaminants contained in a sample to an SPFS sensor section (e.g., a primary antibody, a solid-phase layer or a metal thin film).

Technical Solution

The present inventors conducted studies with a focus on the facts that the generation of nonspecific signals in an immunoassay using SPFS is caused by nonspecific adsorption of contaminants contained in a sample such as plasma and serum to a sensor section and that the contaminants are proteins, lipids and the like other than a compound to be measured. As a result, the present inventors discovered that nonspecific adsorption of contaminants to a sensor section can be suppressed and nonspecific signals (background) originating from the contaminants can be largely reduced by altering (modifying) the structures of the contaminants by a specific treatment method; and that, by minimizing the effects on a compound to be measured and limiting a reduction in the signal originating from the compound to be measured to a relatively low level, the ratio of the value of the signal with respect to the background value (S/B ratio), to which much importance is given in measurement, can be improved, thereby completing the present invention.

That is, in one aspect of the present invention, the method of suppressing nonspecific signals according to the present invention is as follows.

A method of suppressing nonspecific signals originating from contaminants in an immunoassay using surface plasmon-field enhanced fluorescence spectroscopy (SPFS) (including cases where a receptor for a compound to be measured is used in place of a primary antibody), the method being characterized in that it comprises performing at least one of the following pretreatments:

(1) a pretreatment of adding an acid or an alkali to a sample;
(2) a pretreatment of adding a metal ion to the sample; and
(3) a pretreatment of heating the sample.

Advantageous Effects of Invention

According to the present invention, in an immunoassay using SPFS, nonspecific signals (background) generated by nonspecific adsorption of contaminants contained in a sample to an SPFS sensor section can be largely reduced. Further, according to the present invention, the nonspecific signals originating from contaminants can be suppressed by minimizing the effects on a compound to be measured, that is, by limiting a reduction in the signal originating from the compound to be measured to a relatively low level.

Consequently, according to the present invention, in an immunoassay using SPFS, the background noise can be reduced and the ratio of the value of the signal originating from the compound to be measured with respect to the background value (S/B ratio) can be improved even for contaminant-containing samples such as plasma and serum, so that an infinitesimal amount of the compound can be measured more accurately.

The pretreatment(s) used in the present invention require neither a complicated step nor arrangement of a special region on an SPFS sensor chip; therefore, a high effect can be attained without sacrificing the operability and the cost.

DESCRIPTION OF EMBODIMENTS

The present invention relates to a method of suppressing nonspecific signals originating from contaminants in an immunoassay using surface plasmon-field enhanced fluorescence spectroscopy (SPFS). The method of suppressing nonspecific signals according to the present invention will now be described.

1. Compound to be Measured
(1) Sample

The sample to be used in the present invention is not particularly restricted, and examples thereof include blood, serum, plasma, urine, spinal fluid, saliva, cells, tissues and organs that are collected from humans or animals, and preparations thereof (such as biopsy specimens). Particularly, blood, serum and plasma that potentially contain a tumor antigen and a tumor marker are preferred as a biological sample to be measured.

As required, liquid samples such as blood, serum, plasma, urine, spinal fluid and saliva may be diluted with an appropriate buffer prior to use. Solid samples such as cells, tissues and organs can be homogenized with an appropriate buffer and the resulting suspension or supernatant thereof can be used as is or after further dilution.

(2) Compound to be Measured

The compound to be measured may be any substance as long as it can be captured by a ligand (antibody) in an immunoassay. In cases where lectin is used as a fluorescent label in a sandwich method, a substance having a sugar chain is the compound to be measured.

Examples of such a compound to be measured include proteins (including glycoproteins), lipids (including glycolipids), and their modified molecules and complexes, and preferred examples of the compound to be measured include prostate-specific antigens (PSAs) and other tumor markers. It is known that the sugar chain of the PSA of prostate cancer patients comprises sialic acid bound via an $\alpha$-2,3 bond or $\alpha$-2,6 bond.

2. Pretreatments

In the present invention, at least one of the following pretreatments: (i) a pretreatment of adding an acid or an alkali to a sample; (ii) a pretreatment of adding a metal ion to the sample; and (iii) a pretreatment of heating the sample is performed. These pretreatments may be performed individually or in combination. Since these pretreatments are performed so as to inhibit nonspecific adsorption of contaminants contained in a sample to an SPFS sensor section of SPFS, they are performed before supplying the sample to the measurement area of the below-described SPFS measurement apparatus (before bringing the sample into contact with a reaction layer formed on a metal thin film of a sensor chip). The pretreatments will now each be described below.

(1) Pretreatment of Adding Acid or Alkali to Sample

The acid or the alkali to be added is not particularly restricted, and any organic or inorganic acid can be used.

In order to maintain a prescribed pH in a sample, the acid or the alkali is usually added to the sample in the form of a buffer. The buffer can be selected as appropriate in accordance with the intended pH and the buffer may be, for example, a hydrochloric acid-potassium chloride buffer for a pH of 1.0 to 2.2, a glycine-hydrochloric acid buffer for a pH of 2.2 to 3.6, a citrate buffer for a pH of 3.0 to 6.2, an acetate buffer for a pH of 3.0 to 5.6, a citrate-phosphate buffer for a pH of 2.6 to 7.0, a phosphate buffer for a pH of 5.8 to 8.0, a Tris-hydrochloric acid buffer for a pH of 7.2 to 9.0, a glycine-sodium hydroxide buffer for a pH of 8.6 to 10.6, a carbonate-bicarbonate buffer for a pH of 9.2 to 10.6, or a disodium hydrogen phosphate-sodium hydroxide buffer for a pH of 11.0 to 12.0.

The pH of the sample after the addition can be selected in accordance with the sample and the compound to be measured, within a range where nonspecific signals originating from the contaminants contained in the sample are suppressed at a level required for the purpose of the measurement and the reduction in the signal of the compound to be measured is at an acceptable level. Particularly, a sialic acid-containing sugar chain is likely to be cut or undergo other degeneration in a pretreatment with an acid, an alkali or the like (sialic acid bound to an end of a sugar chain is especially likely to be cut); therefore, when the compound to be measured is a glycoprotein or glycolipid having a sialic acid-containing sugar chain, especially when such a compound to be measured is measured using a labeled lectin, it is required to select the pretreatment condition (pH of the sample after the addition) within a range in accordance with the purpose of the pretreatment while taking into consideration the acceptable range of the reduction in the signal of the compound to be measured. Such a range of the pretreatment condition can be evaluated by the method described below in (4) and adjusted as appropriate; however, generally, a pretreatment of adjusting the pH of a sample to be 1 to 4 with an addition of an acid to the sample or a pretreatment of adjusting the pH of a sample to be 8 to 11 with an addition of an alkali to the sample is preferred (see the treatment methods 1 to 5 of Examples 1 and 3).

The treatment time can be selected as appropriate in a range where the effect of the treatment is attained and, for example, the sample may be left to stand for 30 minutes at a prescribed pH and room temperature. Thereafter, as required, the pH and the like of the sample can be restored to the original state by, for example, changing the buffer to physiological saline.

(2) Pretreatment of Adding Metal Ion to Sample

The metal ion to be added may be any metal ion as long as it causes degeneration of contaminants contained in a sample, such as proteins and lipids, and the metal ion is particularly preferably a heavy metal ion. Examples the heavy metal ion include $Pb^{2+}$, $Cr^{3+}$, $Fe^{3+}$, $Fe^{2+}$, $Cd^{2+}$, $Ni^{2+}$, $Hg^{2+}$, $Co^{2+}$, $Sn^{2+}$, $Sn^{4+}$, $Mn^{2+}$, $Mo^{3+}$, $W^{3+}$, $Zn^{2+}$, $Cu^{2+}$ and $Ag^{2+}$. Upon using these metal ions, it is preferred to take into consideration the environmental pollution caused by liquid waste and the like and, from this viewpoint, for example, $Fe^{3+}$ and $Zn^{2+}$ are preferred.

When the compound to be measured is a sugar complex such as a glycoprotein or glycolipid, particularly when the compound to be measured is a glycoprotein or glycolipid having a sialic acid-containing sugar chain, the "pretreatment of adding a metal ion to the sample" is preferred. A sialic acid-containing sugar chain is likely to be cut or undergo other degeneration in a pretreatment with an acid or an alkali or by heating or the like (sialic acid bound to an end of a sugar chain is especially likely to be cut); however, in this respect, metal ions do not affect the sugar chain moieties of glycoproteins and glycolipids and act only on the protein moieties and lipid moieties. Therefore, when the compound to be measured has a sugar chain (particularly when the compound to be measured is a glycoprotein or glycolipid having a sialic acid-containing sugar chain), the "pretreatment of adding a metal ion to the sample" is preferred from the standpoints of inhibiting a change in the structure of the sugar chain of the compound to be measured and suppressing nonspecific adsorption of contaminants. The "pretreatment of adding a metal ion to the sample" is particularly preferred when a compound to be measured having a sugar chain is measured using a labeled lectin in place of a secondary antibody in a sandwich method.

Further, in the "pretreatment of adding a metal ion to the sample", the sample can be pretreated under a neutral condition, and measurement can be performed without any particular effect on the subsequent antigen-antibody reaction. Therefore, after the pretreatment, an immunoassay using SPFS can be performed as is, without removal of the metal ion. Alternatively, as required, the measurement may be performed after removing the added metal ion from the sample by, for example, changing the buffer to physiological saline.

The method of adding a metal ion is not particularly restricted, and a metal ion is usually added in the form of a metal salt. The metal salt can be added as an inorganic acid salt or an organic acid salt, preferably as a water-soluble salt. This water-soluble salt is, for example, a salt of a strong acid. For instance, $Fe^{3+}$ can be added as $FeCl_3$ or $Fe_2(SO_4)_3$, and $zn^{2+}$ can be added as $ZnCl_2$ or $ZnSO_4$.

The concentration at which the metal ion is added can be selected as appropriate taking into consideration the effect of inhibiting adsorption of contaminants as well as the effects on the compound to be measured, and the metal ion is added at a concentration of usually 10 μM to 5 M, preferably 50 μM to 100 mM (see the treatment methods 6 and 7 of Examples 1 and 3).

(3) Pretreatment of Heating Sample

The conditions of the pretreatment of heating the sample can be selected in accordance with the sample and the compound to be measured, within a range where nonspecific signals originating from the contaminants contained in the sample are suppressed at a level required for the purpose of the measurement and the reduction in the signal of the compound to be measured is at an acceptable level. Particularly, a sialic acid-containing sugar chain is likely to be cut or undergo other degeneration in a pretreatment by heating or the like (sialic acid bound to an end of a sugar chain is especially likely to be cut); therefore, when the compound to be measured is a glycoprotein or glycolipid having a sialic acid-containing sugar chain, especially when such a compound to be measured is measured using a labeled lectin, it is required to select the pretreatment conditions (heating temperature and time) within a range in accordance with the purpose of the pretreatment while taking into consideration the acceptable range of the reduction in the signal of the compound to be measured. Such a range of the pretreatment conditions can be evaluated by the below-described method and adjusted as appropriate; however, generally, a pretreatment of heating the sample at 95 to 100° C. for 5 to 10 minutes is preferred (see the treatment method 8 of Examples 2 and 3).

The method of the heat treatment is not particularly restricted and, for example, the sample can be heated using a commercially available heating block at a prescribed temperature for a prescribed time.

(4) Method of Evaluating Effects of Pretreatment Conditions

The effects of the pretreatment conditions can be evaluated by comparing the ratio of the signal against background (S/B) determined for a pretreated sample with the S/B determined for a non-pretreated sample (see Examples and Comparative Example).

Here, the background (B) of a sample refers to a signal value measured by an immunoassay using SPFS for a sample not containing a compound to be measured. The signal (S) of a sample refers to a signal value measured by an immunoassay using SPFS for a sample containing the compound to be measured. The ratio S/B is calculated from the values of these signals (in this case, precisely, the signal (S) is observed as a signal (S+B) in which the background (B) is added to the signal (S); however, since B is smaller than S, the value of S/B is used as the signal ratio against background).

When the S/B value of a pretreated sample (the below-described treatment methods 1 to 7 of Example 1 and treatment method 8 of Example 2) is compared with the S/B value of a non-pretreated sample (the below-described treatment method 9 of Comparative Example 1), if the S/B value of the pretreated sample is larger than the S/B value of the non-pretreated sample, such condition(s) can be used as the pretreatment condition(s) of the present invention. The size of the difference can be determined taking into consideration the purpose of the measurement and is also variable depending on the pretreatment method, the sample, the compound to be measured and the like. For example, in cases where the sample is serum and the compound to be measured is a glycoprotein or a glycolipid and a labeled antibody is used as a secondary antibody in a sandwich method, the ratio of both S/B values, that is, the value of (S/B for pretreated sample)/(S/B for non-pretreated sample), is preferably not less than 1.5, more preferably not less than 2. In cases where the sample and the compound to be measured are the same as described above and a labeled lectin is used in place of a secondary antibody in a sandwich method, the ratio of both S/B values, (S/B for pretreated sample)/(S/B for non-pretreated sample), is preferably not less than 5.0, more preferably not less than 6.0.

In the measurement of the S/B values, as the sample that does not contain a compound to be measured, for example, when the sample is serum, a commercially available serum (normal human pooled serum) can be used. The sample containing a compound to be measured can be prepared by adding a certain amount of a standard product of the compound to be measured (in the case of PSA, it is prepared from a culture supernatant of PSA-producing cells) to the commercially available serum. It is needless to say that the added amount and the like of the commercially available sample and compound to be measured are determined under the same conditions for both the pretreated and non-pretreated samples.

3. Immunoassay Using Surface Plasmon-Field Enhanced Fluorescence Spectroscopy (SPFS)

The present invention employs an immunoassay method in which a fluorescently labeled molecule captured in a sensor section by an antigen-antibody reaction is excited by SPFS and the thus enhanced fluorescence emission is measured. Therefore, the immunoassay method used in the present invention can be any fluoroimmunoassay, and a sandwich method is usually employed. The present invention using a sandwich method will now be described.

(1) Immunoassay
(a) Ligand

The ligand used in the present invention (primary antibody of the sandwich method) is an antibody which specifically recognizes and binds with a compound to be measured. Particularly, the ligand is preferably a monoclonal antibody against the compound to be measured. In the present invention, depending on the compound to be measured, a receptor thereof can also be used as the ligand, and those cases where a receptor of the compound to be measured is used in place of a primary antibody of a sandwich method are also included in the scope of the present invention.

When a tumor antigen, a tumor marker or the like is used as the compound to be measured, it is appropriate to use an antibody (e.g., monoclonal antibody) that specifically binds to the antigen as the ligand. For example, when a human PSA (prostate-specific antigen) is the compound to be measured, an anti-human PSA antibody can be used.

The above-described ligand (primary antibody of a sandwich method) means a substance which specifically captures a compound to be measured and encompasses not only complete antibodies but also arbitrary antibody fragments and derivatives, including complete antibodies as well as various antibodies such as Fabs, Fab'$_2$s, CDRs, humanized antibodies, polyfunctional antibodies and single-chain antibodies (ScFvs).

(b) Immobilization of Ligand

In the present invention, it is required that the compound to be measured be captured through the ligand described in the above (a) and the fluorescently labeled molecule bound to the captured compound be excited by SPFS. Therefore, the ligand is made into a solid phase (immobilized) on a metal thin film of an SPFS sensor section. As a method for the immobilization on the metal thin film, a conventional method can be employed, and the details thereof will be described below in relation to SPFS.

(c) Fluorescent Label

In the present invention, in order to fluorescently label the compound to be measured that is captured through a ligand on a metal thin film of an SPFS sensor section in the process described in the above (b), a secondary antibody, a lectin and a fluorescent label that can be used in an ordinary sandwich method are employed.

As the secondary antibody, for example, a monoclonal antibody which recognizes an epitope different from the one recognized by the ligand (primary antibody) on the compound to be measured can be used to prepare a fluorescently labeled antibody.

Further, in cases where the compound to be measured has a sugar chain, a lectin which binds to the sugar chain with high binding capacity can also be used as a fluorescent label of the sandwich method. Examples of the lectin include ricin B chain-related "R-type lectins", "calnexin/calreticulin", "C-type lectins", "galectins", "leguminous lectins", "L-type lectins", "P-type lectins", "annexins", "I-type lectins" and other various lectins, and a lection suitable for an intended purpose can be selected. For example, WFA (*Wisteria floribunda* lectin), SBA (soybean lectin) or TJA-II (*Trichosanthes japonica* lectin) can be used when the compound to be measured is a prostate-specific antigen (PSA); LCA (*Lens culinaris* lectin), AAL (*Aleuria aurantia* lectin) or AOL (*Aspergillus oryzae* lectin) can be used when the compound to be measured is α-fetoprotein (AFP); and TJA-I (*Trichosanthes japonica* lectin) or the like can be used when the measurement subject is a carcinoembryonic antigen (CEA).

As a method of preparing the fluorescent label, for example, a method in which a carboxyl group is imparted to a fluorescent substance, which carboxyl group is then active-esterified using water-soluble carbodiimide (WSC) and N-hydroxysuccinic acid (NHS), and the thus active-esterified carboxyl group and an amino group contained in an antibody or lectin are subsequently allowed to undergo a dehydration reaction using water-soluble carbodiimide so as to perform immobilization, and the like can be employed.

A fluorescent dye is not particularly restricted; however, in the present invention using SPFS, when performing the below-described fluorescence measurement, it is desired to use a fluorescent dye having a maximum fluorescence wavelength in a wavelength region where light absorption by a metal contained in a metal thin film is limited. For example, in cases where gold is used as the metal thin film, in order to minimize the effect of light absorption by the gold thin film, it is desired to use a fluorescent dye having a maximum fluorescence wavelength of 600 nm or longer. Accordingly, in these cases, it is particularly desirable to use a fluorescent dye having a maximum fluorescence wavelength in the near-infrared region, such as Cy5 or Alexa Fluor (registered trademark) 647. The use of such a fluorescent dye having a maximum fluorescence wavelength in the near-infrared region is useful also when blood is used as a sample because the effect of light absorption by iron originating from the blood cell components in the blood can thereby be minimized. Meanwhile, in cases where silver is used as the metal thin film, it is desired to use a fluorescent dye having a maximum fluorescence wavelength of 400 nm or longer.

(2) Surface Plasmon-Field Enhanced Fluorescence Spectroscopy (SPFS)

Surface plasmon-field enhanced fluorescence spectroscopy (SPFS) is a method which utilizes a phenomenon that, when an excitation light is irradiated to a metal thin film formed on a dielectric member at an angle that causes attenuated total reflection (ATR), an evanescent wave transmitting through the metal thin film is enhanced by several ten times to several hundred times due to resonance with surface plasmon, thereby efficiently exciting a fluorescent material labeling a compound to be measured that is captured in the vicinity of the metal thin film so as to measure its fluorescent signal. Such SPFS is extremely sensitive as compared to common fluorescent labeling methods and the like; therefore, it is capable of quantifying a compound to be measured even when the compound exists in a sample only in a trace amount. When an SPFS method is employed, the measuring member can take any constitution of a flow path or a well, and the sensor chip, reaction layer, SPFS system, SPFS measurement apparatus and the like to be used can be those which are usually used.

The surface plasmon-field enhanced fluorescence spectroscopy (SPFS) used in the present invention will now be described referring to FIGS. 1 and 2; however, the present invention is not restricted thereto, and any method can be employed as long as it utilizes the principles of SPFS.

(a) SPFS Measurement Apparatus

Basically, an SPFS measurement apparatus has a detachable SPFS measuring member and comprises, for example, a light source for irradiating an excitation light (preferably a laser beam) having a wavelength appropriate for the fluorescent material to be used; a prism for allowing the excitation light to enter the backside of a metal thin film of a sensor chip at a prescribed angle (when a planar substrate-form sensor chip is used as a transparent support); a light receiver which receives light reflected by the metal thin film and measures its intensity; a lens for condensing fluorescent light emitted from the fluorescent material; a detector for measuring the intensity of the fluorescent light; and various filters for allowing only a portion of the excitation light and fluorescent light that has a prescribed wavelength to transmit therethrough and cutting other light.

Figure 1:
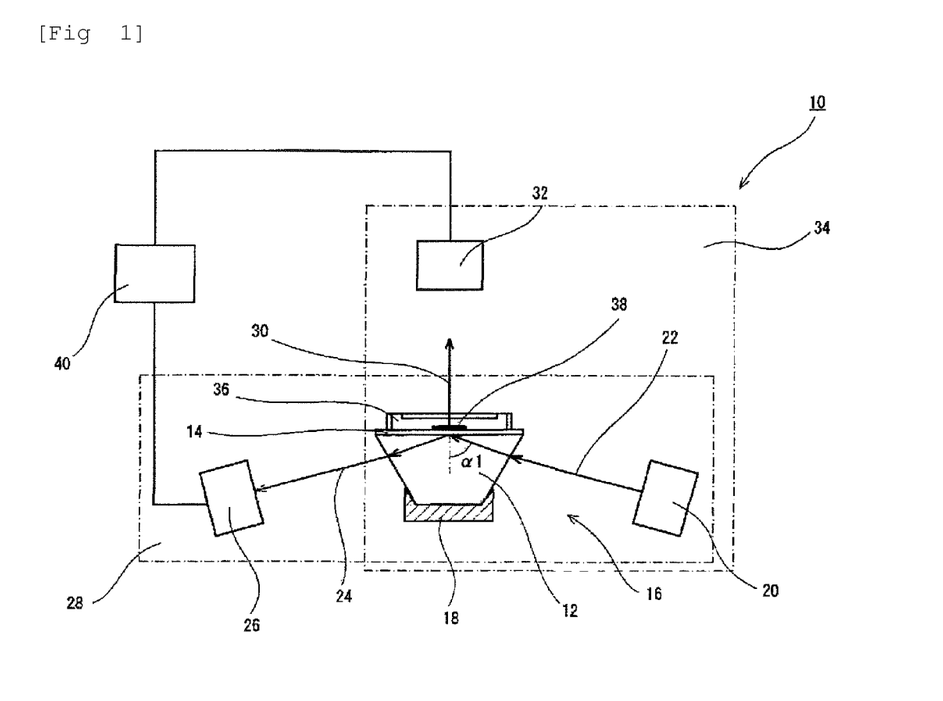
FIG. 1 schematically shows the overall constitution of an SPFS measurement apparatus suitable for the use in the present invention.
Figure 2:
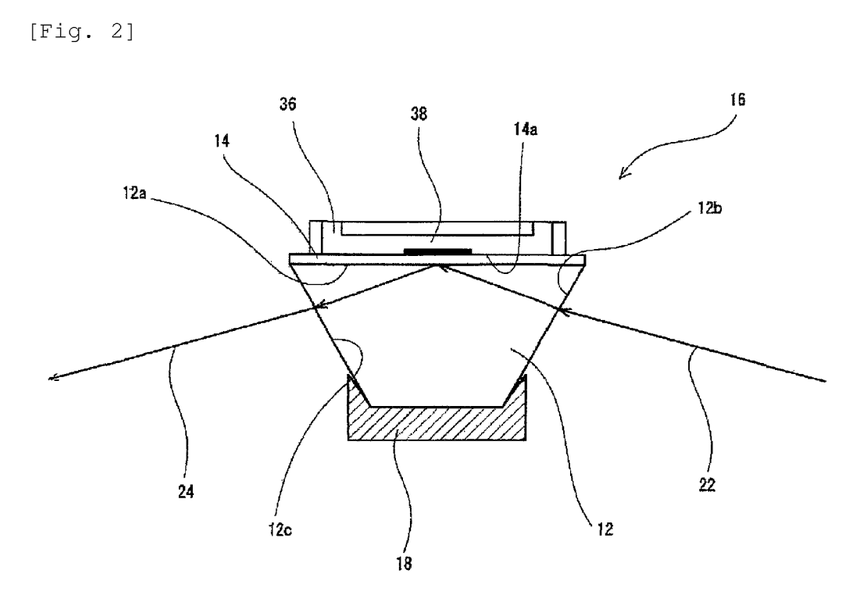
FIG. 2 is a partially enlarged view showing the vicinity of the sensor chip of the measurement apparatus shown in FIG. 1.

Examples of such an SPFS measurement apparatus used in an immunoassay are shown in FIGS. 1 and 2.

FIG. 1 schematically shows the overall constitution of an SPFS measurement apparatus suitable for the use in the present invention. FIG. 2 is a partially enlarged view showing the vicinity of the sensor chip of the measurement apparatus shown in FIG. 1.

As shown in FIGS. 1 and 2, a quantitative measurement apparatus 10 comprises: a prism-shaped dielectric member 12 whose vertical cross-sectional shape is substantially trapezoidal; and a sensor chip 16 having a metal thin film 14 formed on a horizontal upper surface 12a of the dielectric member 12, the sensor chip 16 being mounted to a sensor chip mounting section 18 of the quantitative measurement apparatus 10.

In addition, as shown in FIG. 1, a light source 20 is arranged inferiorly to the dielectric member 12 on the side of a side surface 12b. An incoming light 22 emitted from this light source 20 enters the side surface 12b of the dielectric member 12 from the lower outside of the dielectric member 12 and is irradiated via the dielectric member 12 toward the metal thin film 14 formed on the upper surface 12a of the dielectric member 12.

Between the light source 20 and the dielectric member 12, a polarization filter, which is used for P-polarization of a laser beam emitted from the light source 20 so as to allow surface plasmon to be efficiently generated on the metal thin film 14, may also be arranged.

Further, as shown in FIG. 1, inferiorly to the dielectric member 12 and on the side of the other side surface 12c, a light-receiving means 26, which receives metal thin film-reflected light 24 that is the incoming light 22 reflected by the metal thin film 14, is arranged.

The light source 20 comprises an incidence angle-adjusting means (not shown), which is capable of appropriately altering an incidence angle α1 of the incoming light 22 emitted from the light source 20 with respect to the metal thin film 14. Meanwhile, the light-receiving means 26 also comprises a movable means not shown in the figure and is constituted in such a manner to ensure reception of the metal thin film-reflected light 24 in synchronization with the light source 20 even when the reflection angle of the metal thin film-reflected light 24 is altered.

An SPR measuring section 28 of the quantitative measurement apparatus 10, which performs SPR measurement, is constituted by the sensor chip 16, the light source 20 and the light-receiving means 26.

Further, above the sensor chip 16, a light-detecting means 32, which is used for receiving fluorescence 30 emitted by excitation of the below-described fluorescent substance, is arranged.

Between the sensor chip 16 and the light-detecting means 32, for example, a cut filter or a condenser lens may also be arranged.

An SPFS measurement section 34 of the quantitative measurement apparatus 10, which performs SPFS measurement, is constituted by the sensor chip 16, the light source 20 and the light-detecting means 32.

The light-receiving means 26 and the light-detecting means 32 are each connected to a quantitative calculation means 40 and configured in such a manner that the amount of the metal thin film-reflected light 24 received by the light-receiving means 26 and the amount of the fluorescence 30 received by the light-detecting means 32 are transmitted to the quantitative calculation means 40.

Moreover, in the sensor chip 16 of Examples described below, a flow path 36 is formed on upper surface 14a of the metal film 14. On a part of this flow path 36, a sensor section 38, in which a molecule (ligand) that specifically binds to a compound to be measured (analyte) is immobilized, is arranged.

(b) SPFS Measuring Member

In the above-described SPFS measurement apparatus, the SPFS measuring member generally has a constitution in which a sensor chip, on which an area for forming a sandwich-type immunocomplex and performing fluorescence measurement by SPFS (measurement area) is formed, is laminated with a member for constructing a flow path or well, which is capable of retaining, on the measurement area, a variety of solutions (e.g., a sample containing a compound to be measured, a fluorescent label solution and other reaction reagents) that are used for the formation of the sandwich-type immunocomplex and the like.

The sensor chip basically comprises: a transparent support for introducing an excitation light to the back of a metal thin film; a metal thin film for generating surface plasmon resonance, which is formed on the transparent support; and a reaction layer for capturing a compound to be measured on the sensor surface, which reaction layer is formed on the metal thin film. As required, the sensor chip may further comprise a spacer layer for inhibiting metal quenching of fluorescence caused by excessive proximity of a fluorescent material to the metal thin film, which spacer layer is formed between the metal thin film and the reaction layer.

The part where the reaction layer is formed corresponds to the measurement area. The measurement area may be arranged by forming the reaction layer on the entire bottom surface of the flow path or well, or by forming the reaction layer only on a portion of the bottom surface (with a desired pattern, as required). The size of the measurement area can be adjusted, taking into consideration the irradiation area of the excitation light that is generally a laser beam. For example, when the spot diameter of the excitation light is about 1 mmφ, the assay area is usually designed in such a manner to have a size of at least several millimeters square.

In the case of a "flow path-type" SPFS system in which various solutions are transferred through a closed flow path, the measuring member is constructed by mounting on the sensor chip a "flow cell" having holes for forming a flow path and, as required, further mounting thereon a "top plate" having a liquid inlet port and a liquid outlet port at the positions corresponding to the holes of the flow cell, in such a manner that the flow cell and the top plate are tightly adhered and fixed with each other. The sensor chip surface at the positions corresponding to the holes of the flow cell constitutes the bottom surface of a flow path, on which a measurement area is formed. In such a flow path-type system, for example, by using a liquid transfer means including a pump and a tube, various liquids can be introduced to the flow path via the liquid inlet port and discharged from the liquid outlet port and, as required, the liquids can also be transferred in a reciprocating manner or a circulating manner. The conditions such as the liquid transfer rate and the liquid transfer (circulation) time can be adjusted as appropriate, taking into consideration the sample amount, the analyte concentration in the sample, the size of the flow path or well, the mode of the reaction layer (e.g., the density of immobilized ligand), the pump performance and the like.

Meanwhile, in the case of a "well-type" SPFS system in which various solutions are retained in a space larger than the above-described flow path, the measuring member is constructed by mounting and fixing, on the sensor chip, a "well member" having a through-hole(s) for forming a well(s). In such a well-type system, various liquids can be added to and removed from the well(s) using a pipet-form member or the like.

The flow cell can be made of, for example, a sheet-form polydimethylsiloxane (PDMS). The top plate is prepared from a transparent material so that the fluorescence emitted from the measurement area can be measured, and the top plate can be made of, for example, a plate-form polymethyl methacrylate (PMMA). Alternatively, the flow cell and the top plate can be made of a plastic that is molded or photolithographed into a desired shape.

The means for tightly adhering and fixing the flow cell or well member on the sensor chip is not particularly restricted, and these processes can be generally performed by physical application of pressure from both the top and the bottom. If necessary, an adhesive, a matching oil, a transparent adhesive sheet or the like that has the same light refractive index as that of the transparent support may also be used.

(c) Immobilization of Ligand on Metal Thin Film

As an example of a method for solid-phasing (immobilization) of a ligand on a metal thin film, a method of forming an SAM (Self-Assembled Monolayer) will now be described.

A SAM is formed on the reaction layer side of the metal thin film (on the other surface of the metal thin film that is not in contact with the transparent support (dielectric member in FIGS. 1 and 2)) as a scaffold on which a ligand, preferably a solid-phase layer, is immobilized and for the purpose of inhibiting metal quenching of molecular fluorescence when a plasmon sensor is used in a sandwich assay.

As a monomolecule to be contained in the SAM, a carboxyalkanethiol having about 4 to 20 carbon atoms (available from, for example, Dojindo Laboratories or Sigma-Aldrich Japan) is usually used, and 10-carboxy-1-decanethiol is particularly preferably used. A carboxyalkanethiol having 4 to 20 carbon atoms is suitable because an SAM formed therefrom has small optical influence, that is, the SAM has properties of high transparency, low refractive index, small thickness and the like.

The method of forming such an SAM is not particularly restricted, and a conventionally known method can be employed. Specific examples thereof include a method of immersing a transparent support having a metal thin film formed thereon, on the surface of which metal thin film a layer composed of a mask material is further formed, in an ethanol solution containing 10-carboxy-1-decanethiol (manufactured by Dojindo Laboratories). In this manner, the thiol group of 10-carboxy-1-decanethiol is bound and immobilized with the metal and self-assembled on the surface of the metal thin film to form an SAM.

Further, prior to the formation of SAM, a "spacer layer composed of a dielectric" may be formed. In this case, the monomolecule contained in the SAM is not particularly restricted as long as it is a silane coupling agent which has an ethoxy group (or a methoxy group) that is hydrolyzed to yield a silanol group (Si—OH) and, on the other end, a reactive group such as an amino group, a glycidyl group or a carboxyl group, and a conventionally known silane coupling agent can be used.

The method of forming such an SAM is not particularly restricted, and a conventionally known method can be employed. As a dielectric used for the formation of such a "spacer layer composed of a dielectric", a variety of optically transparent inorganic substances as well as natural or synthetic polymers can be used. Thereamong, silicon dioxide ($SiO_2$), titanium dioxide ($TiO_2$) or aluminum oxide ($Al_2O_3$) is preferably incorporated because of their chemical stability, production stability and optical transparency.

The thickness of the spacer layer composed of a dielectric is usually 10 nm to 1 mm and, from the standpoint of the resonance angle stability, it is preferably 30 nm or less, more preferably 10 to 20 nm. Meanwhile, from the standpoint of electric field enhancement, the thickness of the spacer layer is preferably 200 nm to 1 mm and, from the standpoint of the stability of the electric field-enhancing effect, it is more preferably 400 nm to 1,600 nm.

Examples of a method forming the spacer layer composed of a dielectric include a sputtering method, an electron beam vapor deposition method, a thermal vapor deposition method, a method of forming a spacer layer by chemical reaction using a material such as polysilazane, and a coating method using a spin coater.

The solid-phase layer is formed on the other surface of the SAM that is not in contact with the metal thin film, and the solid-phase layer has a three-dimensional structure.

This "three-dimensional structure" refers to a structure of a solid-phase layer in which immobilization of the below-described ligand is not restricted to the two dimensions of the "sensor substrate" surface (and the vicinity thereof) and can be expanded to the three-dimensional space separate from the substrate surface.

Such a solid-phase layer preferably contains glucose, carboxymethylated glucose and a polymer constituted by at least one monomer selected from the group consisting of monomers included in any of vinyl esters, acrylic acid esters, methacrylic acid esters, olefins, styrenes, crotonic acid esters, itaconic acid diesters, maleic acid diesters, fumaric acid diesters, allyl compounds, vinyl ethers and vinyl ketones, and it is more preferred that the solid-phase layer contain a hydrophilic polymer, such as dextran and a derivative thereof, and a hydrophobic polymer constituted by a hydrophobic monomer(s) included in any of vinyl esters, acrylic acid esters, methacrylic acid esters, olefins, styrenes, crotonic acid esters, itaconic acid diesters, maleic acid diesters, fumaric acid diesters, allyl compounds, vinyl ethers and vinyl ketones. Dextran such as carboxymethyldextran (CMD) is particularly preferred from the standpoints of the biocompatibility, inhibition of nonspecific adsorption reaction and high hydrophilicity.

The molecular weight of CMD is preferably 1 kDa to 5,000 kDa, more preferably 4 kDa to 1,000 kDa.

The solid-phase layer (composed of, for example, dextran or a derivative thereof) preferably has a density of less than 2 $ng/mm^2$. The density of the solid-phase layer can be adjusted as appropriate in accordance with the type of the polymer used therein. It is preferred that the polymer be immobilized on the SAM in such a density range because assay signals are thereby stabilized and increased when a plasmon sensor is used in an assay method. It is noted here that the density of "Sensor Chip CM5" manufactured by Biacore Life Sciences was 2 $ng/mm^2$. The density was estimated to be 2 $ng/mm^2$ as a result of determining the average 2,000 RU for signals that were measured by an SPR-measuring instrument manufactured by Biacore Life Sciences using the CM5 substrate and a substrate having only a gold film.

The average thickness of the solid-phase layer is preferably 3 nm to 80 nm. The average layer thickness can be measured using an atomic force microscope (AFM) or the like. It is preferred that the average thickness of the solid-phase layer be in this range because assay signals are thereby stabilized and increased when a plasmon sensor is used in an assay method.

For a case where carboxymethyldextran (CMD) is used as a polymer contained in the solid-phase layer, a method of immobilization thereof on the SAM surface will now be described concretely.

That is, carboxymethyldextran can be immobilized on an SAM by immersing a substrate, on which a transparent support, a metal thin film and the SAM are laminated in the order mentioned, into MES-buffered saline [MES] which contains 0.01 mg/mL to 100 mg/mL of the above-described carboxymethyldextran preferably having a molecular weight of 1 kDa to 5,000 kDa, 0.01 mM to 300 mM of N-hydroxysuccinimide (NHS) and 0.01 mM to 500 mM of water-soluble carbodiimide (WSC) for a period of 0.2 hours to 3.0 hours.

The density of the resulting solid-phase layer can be adjusted by the number of reaction sites (the number of functional groups of the SAM), the ionic strength and pH of the reaction solution and the WSC concentration with respect to the number of carboxyl groups of the carboxymethyldextran molecules. Further, the average thickness of the solid-phase layer can be adjusted by changing the molecular weight of carboxymethyldextran and the reaction time.

4. Measurement of Subject Compound in Sample

The measurement of the signal of the compound to be measured in a sample can be carried out in accordance with the procedures of an immunoassay using ordinary SPFS. The method of suppressing nonspecific signals originating from contaminants can be used in both a case where the compound to be measured is qualitatively detected and a case where the compound to be measured is quantitatively detected.

In cases where a compound to be measured is quantitatively measured, for example, after adding a standard product of the compound to be measured to a commercially available biological sample (e.g., serum) and subjecting the resultant to the pretreatment(s) of the present invention, the signal is measured to prepare a calibration curve. Then, after subjecting the biological sample to be measured to the same pretreatment(s), the signal is measured and the signal intensity is applied to the calibration curve, thereby the concentration of the compound to be measured can be determined.

EXAMPLES

The present invention will now be described in detail by way of examples thereof; however, the present invention is not restricted thereto.

(Constitution of Quantitative Measurement Apparatus)

In the below-described Examples, as a measurement apparatus, an SPFS measurement apparatus was uniquely produced and used. This SPFS measurement apparatus has the same constitution as the quantitative measurement apparatus 10 described in the above section 3.(2)(a) "SPFS Measurement Apparatus". The symbols used in the following descriptions are also the same as in the above section 3.(2)(a) and FIGS. 1 and 2.

In the above-described constitution, a laser diode (LD) capable of irradiating light having a wavelength of 635 nm was used as the light source 20, and a light attenuation filter (neutral density filter) was arranged as an optical filter between the light source 20 and the dielectric member 12 so that the photon amount can be adjusted.

As the dielectric member 12, a 60° prism manufactured by Sigma Koki Co., Ltd. was used, and the sensor chip 16 was constructed by immobilizing the below-described plasmon excitation sensor above this dielectric member 12.

Further, above the sensor chip 16, an objective lens was arranged as a condenser lens, and a photomultiplier tube (PMT) was used as the light-detecting means 32.

(Preparation of Plasmon Excitation Sensor)

A glass-made transparent planar substrate having a refractive index of 1.72 and a thickness of 1 mm (S-LAL 10, manufactured by Ohara Inc.) was plasma-cleaned, and a chromium thin film was formed on one side of this substrate by a sputtering method. Then, on the surface of the thus formed chromium thin film, a gold thin film was further formed by a sputtering method. The chromium thin film had a thickness of 1 to 3 nm and the gold thin film had a thickness of 44 to 52 nm.

The substrate on which the gold thin film was formed in this manner was immersed in an ethanol solution containing 1 mM of 10-carboxy-1-decanethiol for at least 24 hours to form an SAM film (Self-Assembled Monolayer) on the surface of the gold thin film. The substrate was then removed from the solution and washed with ethanol and isopropanol, followed by drying using an air gun.

Onto this substrate, 0.8 mL of 25 mM MES-buffered saline and 10 mM NaCl solution (pH 6.0), the 25 mM MES-buffered saline containing 0.5 mM of N-hydroxysuccinimide (NHS), 0.5 mM of water-soluble carbodiimide (WSC) and 1 mg/mL of carboxymethyldextran CMD-500-06I4 (manufactured by Meito Sangyo Co., Ltd.: average molecular weight=500,000, degree of substitution=0.51), was applied dropwise and allowed to react for 20 minutes, thereby immobilizing CMD on the SAM.

A polydimethylsiloxane (PDMS) sheet, which had a groove of 0.5 mm in height serving as a flow path as well as a through-hole at both ends of the groove, was disposed on the substrate with the groove facing the CMD film such that the surface of the CMD film was arranged inside the flow path. The PDMS sheet outside the flow path was press-adhered from above, and the PDMS sheet (flow path 36) was screw-fixed with the plasmon excitation sensor.

Immobilization of Antibody

Preparation Example 1

Anti-PSA Antibody-Immobilized Substrate

In the external flow path to which the plasmon excitation sensor was connected as described above, ultrapure water and then phosphate-buffered saline (PBS) were circulated for 10 minutes and 20 minutes, respectively, using a peristaltic pump at a room temperature (25° C.) and a flow rate of 500 μL/min, thereby equilibrating the surface of the plasmon excitation sensor.

Then, after feeding and circulating 5 mL of a phosphate-buffered saline (PBS) containing 50 mM of N-hydroxysuccinimide (NHS) and 100 mM of water-soluble carbodiimide (WSC) for 20 minutes, 2.5 mL of an anti-PSA monoclonal antibody solution (No. 72, 2.5 mg/mL; manufactured by Mikuri Immunolaboratory, Ltd.) was circulated for 30 minutes to immobilize the antibody on the SAM film, thereby preparing an anti-PSA antibody-immobilized SAM film.

Thereafter, by feeding and circulating a phosphate-buffered saline (PBS) containing 1% by weight of bovine serum albumin (BSA) for 30 minutes, a treatment for inhibition of nonspecific adsorption was performed in the flow path.

Preparation of Labeled Antibody and Labeled Lectin

Production Example 1

Fluorescently Labeled PSA Antibody

A fluorescently labeled PSA antibody was produced using a fluorescent substance labeling kit, "Alexa Fluor (registered trademark) 647 Protein Labeling Kit" (manufactured by Invitrogen Corp.). Here, 100-μg equivalent of a PSA antibody (2E2, manufactured by Mikuri Immunolaboratory, Ltd.), 0.1 M sodium bicarbonate and Alexa Fluor 647 reactive dye were mixed and allowed to react at room temperature for 1 hour. Then, the resultant was subjected to gel filtration chromatography and ultrafiltration, thereby removing Alexa Fluor 647 reactive dye that was not utilized in labeling to obtain a fluorescently labeled PSA antibody. Thereafter, the absorbance was measured to quantify the concentration of the fluorescently labeled PSA antibody.

Production Example 2

Fluorescently Labeled WFA Lectin

A fluorescently-labeled WFA lectin was produced using a fluorescent substance labeling kit, "Alexa Fluor (registered trademark) 647 Protein Labeling Kit" (manufactured by Invitrogen Corp.). Here, 100-μg equivalent of a WFA lectin (L-1350, manufactured by Vector Laboratories, Inc.), 0.1 M sodium bicarbonate and Alexa Fluor 647 reactive dye were mixed and allowed to react at room temperature for 1 hour. Then, the resultant was subjected to gel filtration chromatography and ultrafiltration, thereby removing Alexa Fluor 647 reactive dye that was not utilized in labeling to obtain a fluorescently labeled WFA lectin. Thereafter, the absorbance was measured to quantify the concentration of the labeled lectin.

<Measurement of PSA in Serum Sample>

As a sample, a PSA-free pooled human serum was prepared. Further, as a positive sample, a serum sample prepared by adding LNCaP (human prostate cancer cell line) culture supernatant to the PSA-free pooled serum at a PSA concentration of 1 ng/mL was used as a measurement sample in Examples 1 and 2. As the above-described PSA-free pooled human serum, normal human pooled serum was purchased from Kohjin Bio Co., Ltd. and confirmed by ELISA to have a PSA concentration of not higher than 1 pg/mL.

It was examined if various sample pretreatments performed on 50 μL of this substantially PSA-free sample solution showing nonspecific reactions could suppress the nonspecific reactions being observed.

Example 1

Sample Treatment Methods (Acid Treatment (Treatment Methods 1, 2 and 3), Alkali Treatment (Treatment Methods 4 and 5) and Heavy Metal Addition (Treatment Methods 6 and 7))

To 50 μL of the sample solution, 50 μL of the buffer or metal salt solution shown in Table 1 was added and thoroughly stirred in a test tube. After the stirring, the resultant was left to stand at room temperature for 30 minutes. Thereafter, the buffer was changed to physiological saline to obtain a sample for SPFS measurement.

Example 2

Heat Treatment (Treatment Method 8)

To 50 μL of the sample solution, 50 μL of physiological saline was added, and the resultant was subjected to a heat treatment at 100° C. for 5 minutes. The thus heat-treated solution was then left to stand at room temperature to prepare a sample for SPFS measurement.

Comparative Example 1

No Treatment (Treatment Method 9)

A sample for SPFS measurement was prepared by adding 50 μL of physiological saline to 50 μL of the sample solution.

Example 3

Treatment of Positive Sample Solution

The positive sample was also subjected to the same treatments as those performed in Examples 1 and 2 and Comparative Example 1.

TABLE 1

| | Buffer composition | pH after addition of buffer | Final pH |
|---|---|---|---|
| Treatment method 1 | 0.2M hydrochloric acid-potassium chloride buffer, pH 1.0 | pH 1.5 | pH 7.0 |
| Treatment method 2 | 0.1M glycine-HCL, pH 1.5 | pH 2.5 | pH 7.3 |
| Treatment method 3 | 0.1M glycine-HCL, pH 2.5 | pH 3.5 | pH 7.4 |
| Treatment method 4 | 0.1M Tris-HCL, pH 9.0 | pH 8.6 | pH 7.4 |
| Treatment method 5 | 0.1M carbonate-bicarbonate buffer, pH 10.6 | pH 10.2 | pH 7.6 |
| Treatment method 6 | 100 uM $FeCl_3$-PBS(−), pH 7.4 | pH 7.5 | pH 7.5 |
| Treatment method 7 | 100 uM $ZnCl_2$-PBS(−), pH 7.4 | pH 7.7 | pH 7.6 |
| Treatment method 8 | PBS(−), pH 7.4 (heat treatment) | pH 7.6 | pH 7.5 |
| Treatment method 9 | PBS(−), pH 7.4 | pH 7.6 | pH 7.5 |

<Antibody-Antibody Measurement System>

Each measurement sample was allowed to react with the anti-PSA antibody-immobilized substrate (Preparation Example 1) and then brought into contact with the fluorescently labeled PSA antibody (Production Example 1). The details of this process were as follows.

Each measurement sample in an amount of 0.1 mL was added to the flow path and allowed to circulate therein at a flow rate of 200 µL/min for 20 minutes. Then, TBS (TBS-T) containing 0.05% by weight of Tween 20 was fed to wash the flow path for 5 minutes. After the reaction, 0.1 mL of a solution of PSA antibody labeled with Alexa Fluor 647 (in which the PSA antibody was dissolved in phosphate-buffered saline (PBS) at a concentration of 1 µg/mL) was added and allowed to flow in the flow path at a flow rate of 200 µL/min for 5 minutes. Then, TBS (TBS-T) containing 0.05% by weight of Tween 20 was fed again to wash the flow path for 5 minutes. Thereafter, SPFS measurement was performed using the quantitative measurement apparatus.

The results of the SPFS measurement are shown in Table 2. The signal values shown in Table 2 are the values that were actually measured, and the signal values of the PSA-added sera are each shown as "PSA-derived signal value+ background signal value".

TABLE 2

| | Background (B) (value measured for PSA-free serum) | Signal (S) (value measured for PSA-added serum) | S/B | S/B ratio (Note 1) |
|---|---|---|---|---|
| Treatment method 1 | 15300 | 3200000 | 209 | 1.8 |
| Treatment method 2 | 13200 | 3564000 | 270 | 2.4 |
| Treatment method 3 | 14300 | 3770000 | 264 | 2.3 |
| Treatment method 4 | 14200 | 3320000 | 234 | 2.1 |
| Treatment method 5 | 16000 | 3270000 | 204 | 1.8 |
| Treatment method 6 | 15000 | 3749000 | 250 | 2.2 |
| Treatment method 7 | 17400 | 3658000 | 210 | 1.8 |
| Treatment method 8 | 24000 | 2990000 | 125 | 1.1 |
| Treatment method 9 | 34000 | 3892000 | 114 | |

(Note 1)
(S/B determined for pretreated sample)/(S/B determined for non-pretreated sample)

It was confirmed that, by performing a pretreatment having a protein-denaturating effect, the serum background was reduced as compared to the treatment method where the sample was only diluted with physiological saline and the value of S/B was consequently largely improved.

<Antibody-Lectin Measurement System>

Each measurement sample was allowed to react with the anti-PSA antibody-immobilized substrate (Preparation Example 1) and then brought into contact with the fluorescently labeled WFA lectin (Production Example 2). The details of this process were as follows.

Each measurement sample in an amount of 0.1 mL was added to the flow path and allowed to circulate therein at a flow rate of 200 µL/min for 20 minutes. Then, TBS (TBS-T) containing 0.05% by weight of Tween 20 was fed to wash the flow path for 5 minutes. After the reaction, 0.1 mL of a solution of WFA lectin labeled with Alexa Fluor 647 (in which the WFA lectin was dissolved in phosphate-buffered saline (PBS) at a concentration of 1 µg/mL) was added and allowed to flow in the flow path at a flow rate of 200 µL/min for 5 minutes. Then, TBS (TBS-T) containing 0.05% by weight of Tween 20 was fed again to wash the flow path for 5 minutes. Thereafter, SPFS measurement was performed using the quantitative measurement apparatus.

The results of the SPFS measurement are shown in Table 3. The signal values shown in Table 3 are the values that were actually measured, and the signal values of the PSA-added sera are each shown as "PSA-derived signal value+ background signal value".

TABLE 3

| | Background (B) (value measured for PSA-free serum) | Signal (S) (value measured for PSA-added serum) | S/B | S/B ratio (Note 2) |
|---|---|---|---|---|
| Treatment method 1 | 8000 | 200000 | 25 | 4.2 |
| Treatment method 2 | 7300 | 256700 | 35 | 5.8 |
| Treatment method 3 | 8800 | 278000 | 32 | 5.3 |
| Treatment method 4 | 9700 | 250000 | 26 | 4.3 |
| Treatment method 5 | 13000 | 254000 | 20 | 3.3 |
| Treatment method 6 | 9800 | 428000 | 44 | 7.3 |
| Treatment method 7 | 10800 | 410000 | 38 | 6.3 |
| Treatment method 8 | 32000 | 244000 | 8 | 1.3 |
| Treatment method 9 | 72600 | 432000 | 6 | |

(Note 2)
(S/B determined for pretreated sample)/(S/B determined for non-pretreated sample)

It was confirmed that, by performing a pretreatment having a protein-denaturating effect, the serum background was reduced as compared to the treatment method where the sample was only diluted with physiological saline and the value of S/B was consequently largely improved. Further-more, as compared to the treatments with an acid or an alkali, the treatment by an addition of a heavy metal had less effect on the signal, and only the background was successfully reduced.

The invention claimed is:

1. A method of suppressing nonspecific signals originating from contaminants present in a sample to be tested in an immunoassay using surface plasmon-field enhanced fluorescence spectroscopy (SPFS), said method comprising:
performing pretreatment on the sample prior to bringing the sample into contact with a sensor chip, wherein teh pretreatment comprises adding 10 μM to 100 μM of a metal ion to the sample, wherein the metal ion comprises $Pb^{2+}$, $Cr^{3+}$, $Fe^{3+}$, $Fe^{2+}$, $Cd^{2+}$, $Ni^{2+}$, $Hg^{2+}$, $Co^{2+}$, $Sn^{2+}$, $Sn^{4+}$, $Mn^{2+}$, $Mo^{3+}$, $W^{3+}$, $Zn^{2+}$, $Cu^{2+}$ $Ag^{2}$, or a combination thereof:
binding a compound to be measured present in the pretreated sample to a ligand immobilized on a solid phase of the sensor chip without removal of the metal ion from the sample; and
measuring a signal of the sample in the immunoassay.

2. The method of suppressing nonspecific signals according to claim 1, wherein the ratio of a signal against background (S/B), which is determined for said sample subjected to said pretreatment(s), is higher than the ratio S/B determined for said sample not subjected to any of said pretreatment(s).

3. The method of suppressing nonspecific signals according to claim 1, wherein said pretreatment is a pretreatment of adding 10 μM to 100 μM of $Fe^{3+}$ ion or $Zn^{2+}$ ion to said sample.

4. The method of suppressing nonspecific signals according to claim 1, wherein said sample is plasma or serum.

5. The method of suppressing nonspecific signals according to claim 1, wherein said compound to be measured is a glycoprotein or a glycolipid.

6. The method of suppressing nonspecific signals according to claim 1, wherein said compound to be measured is a glycoprotein or glycolipid having a sialic acid-containing sugar chain.

7. The method of suppressing nonspecific signals according to claim 1, wherein
said sample is plasma or serum;
said compound to be measured is a sialic acid-containing glycoprotein or glycolipid; and
said compound to be measured is bound to the ligand on a solid phase of the sensor chip in an SPFS sensor section and is measured using a labeled lectin.

8. The method of suppressing nonspecific signals according to claim 6, wherein said compound to be measured is a prostate-specific antigen (PSA).

9. The method of suppressing nonspecific signals according to claim 2, wherein said pretreatment is a pretreatment of adding 10 μM to 100 μM of $Fe^{3+}$ ion or $Zn^{2+}$ ion to said sample.

10. The method of suppressing nonspecific signals according to claim 2, wherein said pretreatment further comprises heating said sample at 95° C. to 100° C. for 5 to 10 minutes.

11. The method of suppressing nonspecific signals according to claim 2, wherein said compound to be measured is a glycoprotein or a glycolipid.

12. The method of suppressing nonspecific signals according to claim 3, wherein said compound to be measured is a glycoprotein or a glycolipid.

13. The method of suppressing nonspecific signals according to claim 4, wherein said compound to be measured is a glycoprotein or a glycolipid.

14. The method of suppressing nonspecific signals according to claim 2, wherein
said sample is plasma or serum;
said compound to be measured is a sialic acid-containing glycoprotein or glycolipid; and
said compound to be measured is bound to the ligand on a solid phase of the sensor chip in an SPFS sensor section and is measured using a labeled lectin.

15. The method of suppressing nonspecific signals according to claim 3, wherein
said sample is plasma or serum;
said compound to be measured is a sialic acid-containing, glycoprotein or glycolipid; and
said compound to be measured is bound to the ligand on a solid phase of the sensor chip in an SPFS sensor section and is measured using a labeled lectin.

16. A method of suppressing nonspecific signals originating from a contaminant present in a sample to be tested in an immunoassay using surface plasmon-field enhanced fluorescence spectroscopy (SPFS), said method comprising:
performing a pretreatment on the sample, wherein the pretreatment comprises
adding an acid to the sample to adjust the pH of the sample to a pH of 1 to 4, or
adding an alkali to a sample to adjust the of the sample to a pH of 8 to 11, and
restoring the pH of the sample to a pH of 7.0 to 7.6; and
measuring a signal of the sample in the immunoassay.

17. The method of claim 16, wherein the pretreatment is adding the acid to the sample to adjust the pH of the sample to a pH of 1 to 4.

18. The method of claim 17, wherein the acid is in a form of a buffer, and the buffer comprises a hydrochloric acid-potassium chloride buffer, a glycine-hydrochloric acid buffer, or a combination thereof.

19. The method of claim 16, wherein the pretreatment is adding the alkali to a sample to adjust the pH of the sample to a pH of 8 to 11.

20. The method of claim 19, wherein the alkali is in the form of a buffer and the buffer comprises a glycine-sodium hydroxide buffer a carbonate-bicarbonate buffer, or a combination thereof.

* * * * *